United States Patent [19]

Horii et al.

[11] 4,065,615

[45] Dec. 27, 1977

[54] DEOXYAMINOGLYCOSIDE ANTIBIOTIC DERIVATIVES

[75] Inventors: Satoshi Horii, Sakai; Yukihiko Kameda, Toyonaka; Nariakira Mizokami, Suita, all of Japan

[73] Assignee: Takeda Chemical Industries, Ltd., Osaka, Japan

[21] Appl. No.: 487,226

[22] Filed: July 10, 1974

[30] Foreign Application Priority Data

July 12, 1973 Japan .................................. 48-78979

[51] Int. Cl.$^2$ ............................................ C07H 15/22
[52] U.S. Cl. ..................................... 536/10; 424/180; 536/12; 536/17
[58] Field of Search ................. 260/210 AB, 211.5 R, 260/210 R, 210 K, 210 NE; 536/17, 10, 12

[56] References Cited

U.S. PATENT DOCUMENTS

| | | | |
|---|---|---|---|
| 3,678,030 | 7/1972 | Yamazaki et al. | 260/211.5 R |
| 3,826,802 | 7/1974 | Kawaguchi et al. | 260/210 AB |
| 3,923,783 | 12/1975 | Naito et al. | 260/210 AB |
| 3,925,354 | 12/1975 | Umezawa et al. | 260/210 AB |
| 3,932,382 | 1/1976 | Ohki et al. | 536/17 |
| 3,960,833 | 6/1976 | Naito et al. | 536/17 |

OTHER PUBLICATIONS

Umezawa et al., "The Jour. of Antibiotics," vol. XXV, No. 10, 1972, pp. 613-615.

*Primary Examiner*—Johnnie R. Brown
*Attorney, Agent, or Firm*—Wenderoth, Lind & Ponack

[57] ABSTRACT

A new deoxystreptamine-containing aminoglycoside antibiotic derivative in which all the amino groups other than the amino group at the 1-position of the deoxystreptamine moiety are formylated is obtained in a high yield by treating a deoxystreptamine-containing aminoglycoside antibiotic derivative in which all the amino groups are formylated with a basic substance. The new derivatives are very important for production of 1-N-modified deoxystreptamine-containing aminoglycoside antibiotics.

10 Claims, No Drawings

DEOXYAMINOGLYCOSIDE ANTIBIOTIC DERIVATIVES

This invention relates to a process for producing new antibiotic derivatives. More particularly, the invention relates to a process for producing a new deoxystreptamine-containing aminoglycoside antibiotic derivative in which all the amino groups other than the amino groups at the 1-position of the deoxystreptamine moiety are formylated.

It has been known that 1-N-modified deoxystreptamine-containing aminoglycoside antibiotic derivatives are active even against bacteria resistant to the parent antibiotics in which the amino group at the 1-position of the deoxystreptamine moiety is not modified.

Heretofore, a few methods have been reported for selective modification of the amino group at the 1-position of the deoxystreptamine moiety of a deoxystreptamine-containing aminoglycoside antibiotic.

For instance, butirosin B has been synthesized by first producing tetra-N-benzyloxycarbonyl-3',4',2'',3'''-di-O-cyclohexylidene-5''-O-(1-methoxycyclohexyl)ribostamycin from ribostamycin, treating the product with sodium hydride to prepare the 1,6-cyclic carbamate, treating the cyclic carbamate further with barium hydroxide to regenerate the free amino group at the 1-position, including an L-4-phthalimido-2-hydroxybutyryl group into said amino group by acylation and finally removing the masking groups from said amino groups (Journal of Antibiotics 25, 741(1972)).

In another instance, 1-N-(L-4-amino-2-hydroxybutyryl)-kanamycin A has been synthesized by first preparing 6'-N-benzyloxycarbonyl-kanamycin A from kanamycin A, treating the product with N-hydroxysuccinimide ester of L-4-benzyloxycarbonylamino-2-hydroxybutric acid and finally removing benzyloxycarbonyl groups from the amino groups [Journal of Antibiotics, 25, 695 (1972)].

However, the former method requires selective protection of hydroxyl groups of the starting aminoglycoside antibiotics prior to the preparation of the 1,6-cyclic carbamate intermediate. Morever, the method can not be applied to the selective acylation of kanamycin group antibiotics because there is no free hydroxy group at 6-position of their deoxystreptamine group.

In the latter method, a large amount of by-products including positional isomers of the desired 1-N-acyl derivative is produced by acylation in the reaction mixture, and it is very hard to lead the by-products to compounds which can be recycled for use as starting materials of the acylation reaction.

Thus, these known methods are not fully satisfactory in yields, reaction procedures, etc.

The present inventors have quite surprisingly discovered that when the deoxystreptamine-containing aminoglycoside antibiotic derivative in which all the amino groups are formylated is treated with a basic substance such as ammonia, the formylamino group at the 1-position of the deoxystreptamine moiety is deformylated to regenerate the free amino group in a high selectivity and high yield.

Thus, it is an object of this invention to provide a process for producing in a high yield a new deoxystreptamine-containing aminoglycoside antibiotic derivative in which the amino at the 1-position of the deoxystreptamine moiety is free and all the other amino groups are formylated.

Another object is to provide the new deoxystreptamine-containing aminoglycoside antibiotic derivative which is very useful and important as an intermediate for production of 1-N-modified deoxystreptamine-containing aminoglycoside antibiotics.

These and other objects of this invention will be apparent from the detailed description of this invention hereinafter provided.

The parent or starting deoxystreptamine-containing aminoglycoside antibiotics which are to be employed in this invention include xylostasin, ribostamycin, neomycin-group antibiotics (e.g. neomycin A, neomycin B, neomycin C), paromomycin-group antibiotics (.e.g paromomycin I, paromomycin II, mannosyl paromomycin), kanamycin-group antibiotics (e.g. kanamycin A, kanamycin B, kanamycin C) and the 3'-deoxy-and 3',4'-di-deoxyderivatives of these antibiotics, gentamicin-group antibiotics (e.g. gentamicin $C_1$, gentamicin $C_{1a}$, gentamicin $C_2$, sisomicin), lividomycin-group antibiotics (e.g. lividomycin A, lividomycin B), etc.

In accordance with this invention, all the amino groups of such an antibiotic are masked with formyl groups.

The introduction of formyl groups can be carried out by reacting starting material with a formylating agent according to the procedures hitherto known to the chemistry of peptide synthesis for masking of amino groups with formyl groups. For instance, the starting material is reacted with a mixture of formic acid and acetic anhydride, an active ester of formic acid such as p-nitrophenyl formate or a mixed anhydride of formic acid such as acetic formic anhydride.

While the reaction ordinarily proceeds satisfactorily at $-10°$ to $150°$ C, it may be conducted at higher temperature in certain instances.

When use is made of an active ester of formic acid, such reaction solvents as water, dimethylformamide, dioxane, ethylene glycol dimethyl eter, pyridine or the like or a mixture of two or more of such solvents may be employed.

The resultant derivatives of the aminoglycoside antibiotic in which all the amino groups of said starting antibiotic have been formylated is then treated with a basic substance. The basic substance is preferably a weakly basic substance such as ammonia, basic ion-exchange resin, sodium carbonate, potassium carbonate, sodium hydrogen carbonate or potassium hydrogen carbonate. A strongly basic substance such as an alkali hydroxide may also be employed in somewhat reduced quantity.

The reaction is advantageously carried out at the temperature ranging from $0°$ to $150°$ C, more advantageously, at the temperature ranging from $5°$ to $60°$ C.

The solvent may for example be water, dimethylformamide, dioxane, ethylene glycoldimethyl ether or pyridine, or a mixture of two or more thereof.

Thus, new deoxystreptamine-containing aminoglycoside antibiotic derivatives in which, of all the formyl groups of said formyl compound, only the formyl group introduced into the amino group at the 1-position of the deoxystreptamine moiety has been removed are obtained. There are cases where compounds in which the formyl groups introduced into some amino groups other than the amino group at the 1-position have also been removed are obtained as by-products, but these by-products can be recycled for use as starting compounds.

Thus, the method of this invention not only requires a few production steps but also enables the by-products produced in the deformylation reaction to be recycled for use as starting materials, consequently, the desired product can be obtained in good yields. Furthermore, removal of the masking groups in a subsequent step can be easily accomplished without resort to catalytic reduction. Thus, the desired products of this invention are very important as intermediates for production of aminoglycoside antibiotics in which the amino group at the 1-position is modified by, for example, an acyl group such as alpha-hydroxy-omega-masked aminoalkylcarbonyl group.

One of procedures where an alpha-hydroxy-omega-masked aminoalkylcarbonyl group of the formula:

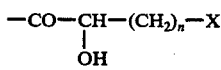

wherein n stands for an integer of 1 to 3 and X is a masked amino group is introduced into the amino group at the 1-position of the deoxystreptamine moiety is set forth below.

The masking group on the amino group may be any of the kinds which have been commonly utilized in the chemistry of peptide synthesis. For instance, phthaloyl, benzyloxycarbonyl, tert.butyloxycarbonyl and trifluoroacetylamino group may be employed.

As a specific procedure for introduction of an alpha-hydroxy-omega-masked aminoalkylcarbonyl group, the abovementioned deformylation product is reacted with a reactive derivative of an alpha-hydroxy-omega-masked amino-carboxylic acid, e.g. an active ester of said acid.

The active ester may be of any known type, such as N-hydroxysuccinimide ester, p-nitrophenyl ester, etc.

This reaction is ordinarily carried out in the presence of a solvent and at a temperature ranging from −20° to 60° C.

Examples of said solvent include water, dimethylformamide, dioxane, chloroform, ethylene glycol dimethyl ether, tetrahydrofuran, pyridine, etc. Thus, a compound in which a group of the above formula has been introduced into theamino group at the 1-position of said deoxystrepamine moiety is obtained.

Then, the compound thus obtained is subjected to an unmasking reaction in which a masking group of masked amino group X and the formyl groups introduced into the amino groups other than the amino group at the 1-position are removed to regenerate free amino groups. This reaction can be performed in accordance with per se known procedures. For example, the compound obtained in the immediately preceding step is treated with a basic substance or an acid salt thereof. Preferably, use is made of amines such as hydrazine, hydroxylamine, etc., their salts such as the corresponding hydrochloride, aetate, etc., and basic ion exchange resins, and also methanolic hydrogen chloride, dilute hydrochloric acid, hydrogen peroxide etc. Removal of the masking group of X and those of the formyl groups may be performed either in a single step or stepwise. The reaction temperature is, preferably 10° to 150° C. The solvent may, for instance, be water or a mixture of water and water-miscible solvent, such as dioxane-water, ethyleneglycol dimethyl ether-water, dimethylformamide-water, etc.

In this manner, there is obtained an aminoglycoside antibiotic in which a group of the formula:

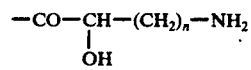

wherein n is an integer of 1 to 3 has been introduced into the amino group at the 1-position of the deoxystreptamine moiety.

Of the thus obtained 1-N-(alpha-hydroxy-omega-aminoalkylcarbonyl) aminoglycoside antibiotics, 3'-deoxybutirosin A and 3'-deoxybutirosin B are new antibiotics and have substantially the same antibacterial activity as those of their parent antibiotics, 3'-deoxyxylostasin and 3'-deoxyribostamycin, respectively, and also are effective against those bacteria which are resistant to their parent antibiotics. Thus, 3'-deoxybutirosin A and 3'-deoxybutirosin B are effective in the treatment of bacterial infections such as urinary tract infections, bronchial pneumonia, pyelonephritis, tonsillitis, etc. Each of these compounds can be administered, either alone or in combination with a vehicle, in such dosate forms as parenteral injections at the normal dose level for adult humans of 100 mg. to 1000 mg. daily.

EXAMPLE 1

In 40 ml. of a mixture of dimethylformamide and water (1:1) are dissolved 2.45 g. of xylostasin and 4.9 g. of p-nitrophenyl formate. The solution is allowed to stand at about 20° C for 20 hours, after which it is concentrated under reduced pressure. Following the addition of ether, the resultant precipitate is recovered by filtration. The precipitate is dissolved in 10 ml. of water and the solution is passed through a column packed with Amberlite CG-50(H+-form, 45 ml.) followed by washing with water. The effluent and washings are pooled and concentrated to dryness under reduced pressure, whereby 2.85 g. of tetra-N-formyl-xylostasin is obtained in a form of white powder.

Thin-layer chromatography (silica gel G; n-propanol-acetic acid-water=2:1:1): Rf 0.50

Thin-layer chromatography (silica gel G; n-propanol-pyridine-acetic acid-water−10:10.05:10) : Rf 0.87

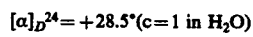

Infrared absorption spectrum (KBR) $\gamma$ : 1660 cm$^{-1}$(C=O) Elemental analysis Calcd. for $C_{21}H_{34}O_{14}N_4$. C, 44.52; H, 6.05; N, 9.89. Found C, 44.16; H, 6.34; N, 9.43.

In 200 ml. of 14% aqueous ammonia is dissolved 2.0 g. of tetra-N-formyl-xylostasin. The solution is allowed to stand at about 20° C for 4 days. The reaction mixture is concentrated to dryness under reduced pressure. The concentrate is dissolved in 10 ml. of water and chromatographed on a column of Amberlite CG-50(NH$_4$+-form, 500 ml.) using water as the developer. The fractions of 3,2',6'-tri-N-formyl-xylostasin are pooled and concentrated to dryness to obtain 520 mg. of white powder.

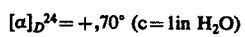

Thin-layer chromatography (silica gel G, n-propanol-acetic acid-water=2:1:1): Rf 0.32

Thin-layer chromatography (silica gel G, n-propanol-pyridine-acetic acid-water=10:10:0.5:10) : Rf 0.47.

EXAMPLE 2

In 15 ml. of a mixture of dimethylformamide and water (1:1) are dissolved 877 mg. of 3'-deoxyxylostasin and 2 g. of p-nitrophenyl formate. The solution is stirred at about 20° C for 20 hours and concentrated under reduced pressure. To the concentrate is added ethyl ether and the resultant precipitate is collected by filtration. The precipitate is dissolved in 5 ml. of water and passed columnwise over Amerlite CG-50($H^+$-form, 50 ml.), followed by washing with water. The effluent and aqueous washings are pooled and concentrated to dryness under reduced pressure, whereby 1.05 g. of tetra-N-formyl-3'-deoxyxylostasin is obtained in a form of white powder.

Thin-layer chromatography (silica gel G, n-propanol-acetic acid-water=2:1:1): Rf 0.57

Thin-layer chromatography (silica gel G, n-propanol-pyridine-acetic acid-water=10:10:0.5:10) : Rf 0.91

$[\alpha]_D^{24} = +28.5°$(c32 1 in $H_2O$)

Infrared absorption spectrum (KBr): $\gamma$ 1660 cm$^{-1}$ (C=O)

Elemental analysis Calcd. for $C_{21}H_{34}O_{13}N_4$. C, 45,82; H, 6.22; N, 10.18. Found C, 44.61; H, 6.45; N, 9.81.

In 100 ml. of 1.0% aqueous ammonia is dissolved 900 mg. of tetra-N-formyl-3'-deoxyxylostasin. The solution is allowed to stand at about 20° C for 6 days. The reaction mixture is concentrated to dryness under reduced pressure. The concentrate is dissolved in 10 ml. of water and the solution is chromatographed on a column of Amberlite CG-50 ($NH^+_4$-form, 200 ml.) using water as the developer. The fractions of 3,2',6'-tri-N-formyl-3'-deoxyxylostasin are pooled and concentrated under reduced pressure whereby 210 mg. of white powder is obtained.

Thin-layer chromatography (silica gel G, n-propanol-acetic acid-water=2:1:1): Rf 0.37

Thin-layer chromatography (silica gel G, n-propanol-pyridine-acetic acid-water=10:10:0.5:10) : Rf 0.67

$[\alpha]_D^{24} = +7.5°$(c=1 in $H_2O$)

EXAMPLE 3

In 10 ml. of a mixture of dimethylformamide and water (1:1) are dissolved 500 mg. of 3'-deoxyribostamycin and 1.5 g. of p-nitrophenyl formate. The solution is allowed to stand at about 20° C for 20 hours. The reaction mixture is concentrated under reduced pressure. Following the addition of ethyl ether, the resultant precipitate is recovered by filtration. The precipitate is dissolved in 5 ml. of water and passed columnwise over Amberlite CG-50 ($H^{30}$-form, 50 ml.) followed by washing with water. The effluent and aqueous washings are pooled and concentrated to dryness under reduced pressure, whereby 580 mg. of tetra-N-formyl-3'-deoxyribostamycin is obtained in a form of white powder.

Thin-layer chromatography (silica gel G, n-propanol-acetic acid-water=2:1:1): Rf 0.51

$[\alpha]_D^{24} = +39.4°$(c=1 in $H_2O$)

Elemental analysis Calcd. for $C_{21}H_{34}O_{13}N_4$. C, 45.82; H, 6.22; N, 10.18. Found C, 44.90; H, 6.51; N, 9.98.

In 50 ml. of 1.0% aqueous ammonia is dissolved 500 mg. of tetra-N-formyl-3'-deoxyribostamycin. The solution is allowed to stand at about 20° C for 6 days and concentrated to dryness under reduced pressure. The concentrate is dissolved in 5 ml. of water and chromatographed on a column of Amberlite CG-50($NH_4^+$-form, 100 ml.) using water as the developer. The fractions of 3,2',6'-tri-N-formyl-3'-deoxyribostamycin are pooled and concentrated to dryness under reduced pressure, whereby 114 mg. of white powder is obtained.

Thin-layer chromatrography (silica gel G, n-propanol-acetic acid-water=2:1:1): Rf 0.36

$[\alpha]_D^{24} = +11.0°$(c=1 in $H_2O$)

EXAMPLE 4

In 50 ml. of a mixture of dimethylformamide and water (1:1) are dissolved 2.0 g. of kanamycin A and 4 g. of p-nitrophenyl formate. The solution is allowed to stand at about 20° C for 16 hours and concentrated under reduced pressure. To the concentrate is added ether and the resultant precipitate is recovered by filtration. The precipitate thus obtained is dissolved in 10 ml. of water and passed columnwise over Amberlite CG-50($H^+$-form, 50 ml.). The effluent and aqueous washings are pooled and concentrated to dryness under reduced pressure, whereby 2.3 g. of tetra-N-formyl-kanamycin A is obtained in a form of white powder.

Thin-layer chromatography (silica gel G, n-propanol-acetic acid-water=2:1:1): Rf 0.41

$[\alpha]_D^{24} = +93.5°$(c=1 in $H_2O$)

Elemental analysis: Calcd. for $C_{22}H_{36}O_{15}N_4$. C, 44.29; H, 6.08; N, 9.39. Found C, 43.86; H, 6.22; N, 9.10.

In 500 ml. of water is dissolved 5 g. of tetra-N-formyl-kanamycin A and, then, 10 ml. of Amberlite IRA-410 ($OH^-$-form) is added. The mixture is reacted with stirring at about 20° C for 8 hours and filtered to remove the resin. The filtrate is concentrated to dryness under reduced pressure and the residue is dissolved in 50 ml. of water and chromatographed on a column of Amberlite CG-50 ($NH_4^+$-form, 500 ml.) using water as the developer. The fractions of 3,6',3''-tri-N-formyl-kanamycin A are pooled and concentrated to dryness under reduced pressure, whereby 1.1 g. of white powder is obtained.

Thin-layer chromatography (silica gel G: n-propanol-acetic acid-water=2:1:1): Rf 0.29

$[\alpha]_D^{24} = +119.1°$(c=1 in $H_2O$)

EXAMPLE 5

In 150 ml. of a mixture of dimethylformamide and water (1:1) are dissolved 6.0 g. of ribostamycin and 12.0 g. of p-nitrophenyl formate. The solution is allowed to stand at about 20° C for 20 hours and concentrated under reduced pressure. To the concentrate is added ether and the resultant precipitate is recovered by filtration. The precipitate is dissolved in 30 ml. of water and passed columnwise over Amberlite CG-50 ($H^+$-form, 160 ml.) followed by washing with water. The effluent and aqueous washings are pooled and concentrated to dryness under reduced pressure, whereby 7.0 g. of tetra-N-formyl-ribostamycin is obtained in a form of white powder.

Thin-layer chromatography (silica gel G, n-propanol-acetic acid-water=2:1:1): Rf 0.54

$[\alpha]_D^{24} = +39.7°$(c =1 in $H_2O$)

Infrared absorption spectrum (KBr): 1660cm$^{-1}$ (C=O)

Elemental analysis: Calcd. for $C_{21}H_{34}N_4O_{14}$; C, 44.52; H, 6.05; N, 9.89. Found: C, 43.84; H, 6.31; N, 9.53.

In 500 ml. of 1% aqueous ammonia is dissolved 5.0 g. of tetra-N-formyl-ribostamycin and the solution is allowed to stand at about 20° C for 6 days and then concentrated to dryness under reduced pressure. The concentrate is dissolved in 25 ml. of water and chromatographed on a column of Amberlite CG-50(NH$_4$+-form 250 ml.) using water as the developer. The fractions of 3,2',6'-tri-N-formyl-ribostamycin are pooled and concentrated to dryness under reduced pressure, whereby 1.25 g. of white powder is obtained.

Thin-layer chromatography (silica gel G, n-propanol-acetic acid-water=2:1:1): Rf 0.39

$[\alpha]_D^{24} = +18.8°(c=1$ in $H_2O)$

EXAMPLE 6

In 125 ml. of a mixture of dimethylformamide and water (1:1) are dissolved 5.0 g. of kanamycin B and 10.0 g. of p-nitrophenyl formate. The solution is stirred at about 20° C for 16 hours and then, concentrated under reduced pressure. To this concentrate is added ether, and the resultant precipitate is recovered by filtration. The precipitate is dissolved in 25 ml. of water and passed columnwise over Amberlite CG-50(H+-form, 150 ml.) followed by washing with water. The effluent and washings are pooled and concentrated in dryness to obtain 5.9 g. of penta-N-formyl-kanamycin B in a form of white powder.

Thin-layer chromatography (silica gel G, n-propanol-acetic acid-water=2:1:1): Rf 0.47

$(\alpha)_D^{24} = +119°(c=1$ in $H_2O)$

Elemental analysis: Calcd. for $C_{23}H_{37}N_5O_{15}$ C, 44.30; H, 5.98; N, 11.23. Found: C, 43.11; H, 6.26; N, 10.73.

In 250 ml. of 1% aqueous ammonia is dissolved 2.5 g. of penta-N-formyl-kanamycin B and the solution is allowed to stand at about 20° C for 7 days. The resultant mixture is concentrated to dryness under reduced pressure. The concentrate is dissolved in 25 ml. of water and chromatographed on a column of Amberlite CG-50(NH$_4$+ − form, 250 ml.) using water as the developer. The fractions of 3,2',6',3''-tetra-N-formyl-kanamycin B are pooled and concentrated to dryness to obtain 530 mg. of white powder.

Thin-layer chromatography (silica gel G, n-propanol-acetic acid-water=2:1:1): Rf 0.37

$(\alpha)_D^{25} = +100.5°(c=1$ in $H_2O)$

EXAMPLE 7

In 20 ml. of a mixture of dimethylformamide and water (1:1) are dissolved 0.80 g. of 3'-deoxykanamycin B and 2.4 g. of p-nitrophenyl formate. The solution is allowed to stand at about 20° C for 16 hours. The resultant mixture is concentrated under reduced pressure. To the concentrate is added ether and then the resultant precipitate is recovered by filtration. The precipitate is dissolved in 5 ml. of water and passed columnwise over Amberlite CG-50(H+-form, 50 ml.) followed by washing with water. The effluent and washings are pooled and concentrated to dryness under reduced pressure, whereby 0.94 g. of penta-N-formyl-3'-deoxykanamycin B is obtained in a form of white powder.

Thin-layer chromatography (silica gel G, n-propanol-acetic acid-water=2:1:1): Rf 0.44

$(\alpha)_D^{25} = +113.3°(c=1$ in $H_2O)$

Elemental analysis: Calcd. for $C_{23}H_{37}N_5O_{14}$ C, 45.47; H, 6.14; N, 11.53. Found: C, 44.21; H, 6.38; N, 11.19.

In 100 ml. of 1% aqueous amonia is dissolved 0.8 g. of penta-N-formyl-3'-deoxykanamycin B and the solution is allowed to stand at about 20° C for 7 days. The resultant mixture is concentrated under reduced pressure. The concentrate is dissolved in 10 ml. of water and chromatographed on a column of Amberlite CG-50(NH$_4$+-form, 100 ml.) using water as the developer. The fractions of 3,2',6',3''-tetra-N-formyl-3'-deoxykanamycin B are pooled and concentrated to dryness, whereby 168 mg. of white powder is obtained.

Thin-layer chromatography (silica gel G, n-propanol-acetic acid-water=2:1:1): Rf 0.32

$(\alpha)_D^{25} = +116.7°(c=1$ in $H_2O)$

EXAMPLE 8

In 75 ml. of N,N-dimethylformamide is suspended 15.0 g. of xylostasin. To the suspension is added 30 ml. of acetic formic anhydride dropwise under ice-cooling and stirring. The mixture is stirred at room temperature for 16 hours and concentrated. The addition of ethyl acetate to the residue yields 21.8 g. of per-N,O-formylxylostasin as precipitates.

Thin-layer chromatography (silica gel G; n-propanol-pyridine-acetic acid-water=10:10:0.5:10): Rf 0.91

Infrared absorption spectrum (KBr) $\nu$ max cm$^{-1}$: 1660(—CO—NH—), 1730(—CO—O—)

$(\alpha)_D^{22} = +29.0°$ $(c=1, H_2O)$

In 100 ml. of 1% aqueous ammonia is dissolved 2.0 g. of per-N,O-formylxylostasin. The solution is allowed to stand at room temperature for 2.5 hours and then neutralized to pH 6.0 with acetic acid. The solution is passed through a column packed with 100 ml. of activated charcoal followed by washing with water and 10% aqueous methanol. The column is eluted with 50% aqueous methanol and the effluent is concentrated under reduced pressure. The freeze-drying of the concentrate gives 1.7 g. of N-tetraformyl-xylostasin (Rf 0.87)*. This substance can be converted to 3,2',6'-tri-N-formylxylostasin after the manner in Example 1.

3,2',6'-tri-N-formylxylostasin can also be derived directly from per-N,O-formylxylostasin by the following manner.

In 1.3 l. of 10% aqueous ammonia is dissolved 13.0 g. of per-N,O-formylxylostasin and the solution is allowed to stand at about 20° C for 5 days. The mixture is concentrated to dryness under reduced pressure. The residue is dissolved in 10 ml. of water and the solution is chromatographed on a column packed with Amberlite CG-50(NH$_4$+-form, 2 l.) using water as the developer, whereby tetra-N-formylxylostasin (Rf 0.87)*, 0.15 g. of 1,2',6'-tri-N-formylxylostasin (Rf 0.58)*, 2.5 g. of 3,2',6'-tri-N-formylxylostasin (Rf 0.47)* and 0.68 g. of 1,3,6'-tri-N-formylxylostasin (Rf 0.71)* are eluted in that order. The chromatography is continued using 2% aqueous ammonia in place of water, whereby 1,3,2'-triformyl-xylostasin (Rf 0.52)*, di-N-formyl-xylostasin, mono-N-formyl-xylostasin, etc. are eluted. The fractions of tetra-N-formyl-xylostasin include ammonium formate. To eliminate ammonium formate, the fractions are adjusted to pH 6.5 with acetic acid, adsorbed on the column packed with activated charcoal, washed with water and 10% aqueous methanol, and then, eluted with 50% aqueous methanol. The effluent is concentrated to dryness under reduced pressure and lyophilized, whereby 2.3 g. of tetra-N-formyl-xylostasin is obtained.

The fractions of the deformylated compounds other than the desired 3,2',6'-tri-N-formyl-xylostasin are combined and concentrated to dryness under reduced pressure. 3.6 g. of the residue is suspended in N,N-dimethylformamide and then, 1.2 ml. of acetic formic anhydride is added dropwise under cooling and stirring. The mixture is stirred at room temperature for 6 hours and concentrated under reduced pressure, followed by addition of ethyl acetate, whereby 4.1 g. of per-N,O-formyl-xylostasin is obtained.

Thus obtained per-N,O-formyl-xylostasin and tetra N-formyl-xylostasin can be employed as starting material for production of 3,2',6'-tri-N-formyl-xylostasin.
*Rf value of thin-layer chromatography: Silica gel G; n-propanol-pyridine-acetic acid-water=10:10:0.5:10.

EXAMPLE 9

In 2.6 l. of 10% aqueous ammonia is dissolved 26.0 g. of tetra-N-formyl-3'-deoxyxylostasin and the solution is allowed to stand at room temperature for 5 days and then concentrated to dryness under reduced pressure. The residue is dissolved in 20 ml. of water and chromatographed on a column of Amberlite CG-50($NH_4^+$-form, 4 l.) using water as the developer, whereby unreacted tetra-N-formyl-3'-deoxy-xylostasin, one of positional isomers of the desired 3,2',6'-tri-N-formyl-3'-deoxyxylostasin, 5.9 g. of 3,2',6'-tri-N-formyl-3'-deoxyxylostasin and another positional isomer of 3,2',6'-tri-N-formyl derivative are eluted in that order.

The chromatography is continued using 2% aqueous ammonia in place of water, whereby other tri-N-formyl derivatives, di-N-formyl derivatives and mono-N-formyl derivatives are eluted.

The fractions of tetra-N-formyl-3'-deoxyxylostasin are purified after the manner in Example 8 and 4.8 g. of the desired product is obtained.

The fractions of the deformylated compounds other than the desired 3,2',6'-tri-N-formyl-3'-deoxyxylostasin are combined and concentrated to dryness under pressure. 11.5 g. of the residue thus obtained is suspended in 60 ml. of N,N-dimethylformamide and then 4.0 ml. of acetic formic anhydride is added dropwise under ice-cooling and stirring. The mixture is stirred at room temperature for 6 hours and concentrated under reduced pressure, followed by addition of ethyl acetate, whereby 12.7 g. of per-N,O-formyl-3'-deoxyxylostasin is obtained.

Thus obtained per-N,O-formyl-3'-deoxyxylostasin and tetra-N-formyl-3'-deoxyxylostasin can be employed as starting material for production of 3,2',6'-tri-N-formyl-3'-deoxyxylostasin.

REFERENCE EXAMPLE 1

In 20 ml. of dimethylformamide are dissolved 800 mg. of 3,2',6'-tri-N-formyl-xylostasin and 800 mg. of N-hydroxysuccinimide ester of L-4-phthalimido-2-hydroxybutyric acid. The solution is allowed to stand at about 20° C overnight and then, concentrated under reduced pressure. Following the addition of ethyl acetate, the precipitate formed is recovered by filtration. The precipitate is dissolved in 50 ml. of 80% ethanol containing 2% of hydrazine hydrate and the solution is allowed to stand at about 20° C overnight. The reaction mixture is filtered to remove the precipitate and the filtrate is concentrated under reduced pressure to remove the ethanol. To the resultant concentrate is added 50 ml. of a 5% aqueous solution of hydrazine hydrate and the mixture is adjusted to pH 6.0 with acetic acid and refluxed for 5 hours. The addition of water to the reaction mixture and the concentration under reduced pressure are repeated and, the residue is dissolved in 100 ml. of water. The solution is run onto a column of CM-Sephadex ($NH_4^+$-form, 130 ml.). After washing with water, elution is carried out with 0.4% aqueous ammonia. The fractions of butirosin A are pooled and concentrated to dryness under reduced pressure to recover 560 mg. of a white powder.

Thin-layer chromatography (silica gel G, the upper layer of the mixture of chloroform-methanol-17% aqueous ammonia: 2:1:1): Rf 0.28

$(\alpha)_D^{24} = +23.7 (c=1 \text{ in } H_2O)$

Infrared absorption spectrum (KBr): 3370, 2938, 1650, 1580, 1345, 1100, 1026 cm$^{-1}$ Elemental analysis: Calcd. for $C_{21}H_{41}O_{12}N_5$ C, 45.40; H, 7.44; N, 12.61. Found: C, 44.64; H, 7.45; N, 12.31.

REFERENCE EXAMPLE 2

In 20 ml. of dimethylformamide are dissolved 300 mg. of 3,2',6'-tri-N-formyl-3'-deoxyxylostasin and 350 mg. of N-hydroxysuccinimide ester of L-4-phthalimido-2-hydroxybutyric acid. The solution is allowed to stand at about 20° C overnight, and then concentrated under reduced pressure. To the concentrate is added ethyl acetate and the resultant precipitate is recovered by filtration and dissolved in 30 ml. of a 10% aqueous hydrazine hydrate. The solution is adjusted to pH 6.0 with acetic acid and, then, refluxed for 16 hours. The precipitate formed is filtered off. The filtrate is diluted with water to 200 ml. and passed column-wise over Amberlite CG-50($NH_4^+$-form, 50 ml.). After the column is washed with 250 ml. of water, the elution is carried out with 0.8% aqueous ammonia. The fractions of 3'-deoxybutirosin A are pooled and concentrated under reduced pressure to obtain 254 mg. of white powder.

Thin-layer chromatography (silica gel G, the upper layer of the mixture of chloroform-methanol-17% aqueous ammonia=2:1:1):Rf 0.30

$(\alpha)_D^{24} = +24.3° (c=1 \text{ in } H_2O)$

Infrared absorption spectrum (KBr): 3370, 2935, 1650, 1580, 1345, 1100, 1026cm$^{-1}$ Elemental analysis: Calcd. for $C_{21}H_{41}O_{11}N_5$ C, 46.74; H, 7.66; N, 12.98. Found: C, 45.59; H, 7.71; N, 12.67.

REFERENCE EXAMPLE 3

In 5 ml. of dimethylformamide are dissolved 100 mg. of 3,2',6'-tri-N-formyl-3'-deoxyribostamycin and 130 mg. of N-hydroxysuccinimide eser of L-4-phthalimido-2-hydroxybutyric acid. The solution is allowed to stand at about 20° C overnight. The reaction mixture is concentrated to dryness under reduced pressure, and, following the addition of ethyl ether, the precipitate formed is recovered by filtration. The precipitate is dissolved in 15 ml. of a 10% aqueous hydrazine hydrate and the solution is adjusted to pH 6.0 with acetic acid. The solution is refluxed for 16 hours and the precipitate formed is filtered off. The filtrate is diluted with water to 100 ml. and run onto a column of Amberlite CG-50($NH_4^+$-form, 50 ml.). The column is washed with 250 ml. of water and, then, with 50 ml. of 0.4% aqueous ammonia. The elution is carried out with 0.8% aqueous ammonia. The fractions of 3'-deoxybutirosin B are pooled and concentrated to dryness under reduced pressure to obtain 82 mg. of white powder.

Thin-layer chromatography (silica gel G: the upper layer of the mixture of chloroform-methanol-17% aqueous ammonia =2:1:1): Rf 0.29

$(\alpha)_D^{24} = +31.8°(c=1$ in $H_2O)$

Infrared absorption spectrum (KBr): 3370, 2935, 1650, 1580, 1345, 1100, 1026cm$^{-1}$ Elemental analysis: Calcd. for $C_{21}H_{41}O_{11}N_5$ C, 46.74; H, 7.66; N, 12.98. Found: C, 45.61; H, 8.02, N, 12.23.

REFERENCE EXAMPLE 4

In 10 ml. of dimethylformamide are dissolved 300 mg. of 3,6',3''-tri-N-formyl-kanamycin A and 300 mg. of N-hydroxysuccinimide ester of L-4-phthalimido-2-hydroxybutyric acid. The solution is allowed to stand at about 20° C overnight and concentrated under reduced pressure. Ethyl acetate is added to the concentrate and the precipitate formed is dissolved in 30 ml. of a 10% aqueous solution of hydrazine hydrate. The solution is adjusted to pH 6.0 with acetic acid and refluxed for 6 hours. The precipitate formed is filtered off. The filtrate is diluted to 300 ml. with water and run onto a column of Amberlite CG-50($NH_4^+$-form, 50 ml.). The column is washed with 250 ml. of water and, then, with500 ml. of 0.4% aqueous ammonia, followed by elution with 0.8% aqueous ammonia. The fractions of 1-N-(L-4-amino-2-hydroxybutyryl)-kanamycin A are pooled and concentrated to dryness under reduced pressure, whereby 244 mg. of white powder is obtained.

Thin-layer chromatography (silica gel G; the upper layer of the mixture of chloroform-methanol-17% aqueous ammonia=2:1:1):Rf 0.24

$(\alpha)_D^{24} = +87.7°(c=1$ in $H_2O)$

Infrared absorption spectrum (KBr): 3400, 2935, 1650, 1570, 1345, 1090, 1025 cm$^{-1}$ Elemental analysis: Calcd. for $C_{22}H_{43}N_5O_{13}.2H_2O$. C, 42.51; H, 7.62; N, 11.27. Found: C, 42,65; H, 7.81; N, 11.35.

REFERENCE EXAMPLE 5

In 15 ml. of dimethylformamide are dissolved 500 mg. of 3,2',6'-tri-N-formylribostamycin and 500 mg. of N-hydroxysuccinimide ester of L-4-phthalamide-2-hydroxybutyric acid. The solution is allowed to stand at about 20° C overnight and, then, concentrated under reduced pressure. Ethyl acetate is added to the concentrate and the precipitate formed is recovered by filtration. The precipitate is dissolved in 50 ml. of 10% aqueous solution of hydrazine hydrate. The solution is adjusted to pH 6.0 with acetic acid and refluxed for 6 hours. The precipitate formed is removed by filtration. The filtrate is diluted with 500 ml. of water and run onto the column of Amberlite CG-50 ($NH_4^+$-form, 100 ml.). The column is washed with 500 ml. of water and 500 ml. of 4% aqueous ammonia, followed by elution with 0.8% aqueous ammonia. The fraction of butirosin B are pooled and concentrated under reduced pressure to obtain 402 mg. of white powder.

Thin-layer chromatography: (silica gel G; the upper layer of a mixture of chloroform-methanol-17% aqueous ammonia =2:1:1) Rf 0.31

The chromatography of butirosin A, 3'-deoxybutirosin A and 3'-deoxybutirosin B conducted simultaneously on one and the same plate gives Rf values of 0.32, 0.31 and 0.31, respectively.

(silica gel G; chloroform-methanol-28% aqueous ammonia-water=1:4:2:1) Rf 0.17

$[\alpha]_D^{24} = +31.0°(c=1$ in $H_2O)$

Infrared absorption spectrum (KBr): $\nu$ 1650cm$^{-1}$ (C=O)

Elemental analysis: Calcd. for $C_{21}H_{41}N_5O_{12}.2H_2O$. C, 42.63; H, 7.67; N, 11.84. Found: C, 42.83; H, 7.51; N, 11.44.

REFERENCE EXAMPLE 6

According to the same manner as that of Reference example 5, 383 mg. of 1-N-(L-4-amino-2-hydroxybutyryl)-kanamycin B is obtained in a form of white powder from 500 mg. of 3,2',6',3''-tetra-N-formyl-kanamycin B and 600 mg. of N-hydroxysuccinimide ester of L-4-phthalimide-2-hydroxybutyric acid.

Thin-layer chromatography: (silica gel G, the upper layer of the mixture of chloroform-methanol-17% aqueous ammonia =2:1:1) Rf 0.29, (silica gel G, chloroform-methanol-28% aqueous ammonia-water=7:4:2:1) Rf 0.15

$[\alpha]_D^{25} = +84.1°(c=1$ in $H_2O)$

Infrared absorption spectrum (KBr):$\nu$1650cm$^{-1}$(C=O)

Elemental analysis: Calcd. for $C_{22}H_{44}H_6O_{12}.2H_2CO_3$. C, 40.68; H, 6.83; N, 11.86. Found: C, 40.14; H, 6.77; N, 11.61.

REFERENCE EXAMPLE 7

According to the same manner as that of Reference example 5, 60 mg. of 1-N-(L-4-amino-2-hydroxybutyryl)-3'-deoxykanamycin B is obtained in a form of white powder from 85 mg. of 3,2',6',3''-tetra-N-formyl-3'-deoxykanamycin B and 100 mg. of N-hydroxysuccinimide ester of L-4-phthalimido-2-hydroxybutyric acid.

Thin-layer chromatography: (silica gel G; the upper layer of a mixture of chloroform-methanol-17% aqueous ammonia =2:1:1) Rf 0.30, (silica gel g, chloroform-methanol-28% aqueous ammonia-water=1:4:2:1) Rf 0.15

$[\alpha]_D^{25} = +75.4°(c=1$ in $H_2O)$

Infrared absorption spectrum (KBr):$\nu$1650cm$^{-1}$(C=0)

Elemental analysis: Calcd. for $C_{22}H_{44}N_6O_{11}.2H_2CO_3$. C, 41.62; H, 6.98; $N_{12.13}$. Found: C, 41.11; H, 6.92; N, 11.78.

What is claimed is:
1. A compound in which all the amino groups other than the amino group at the 1-position on the deoxystreptamine moiety of an aminoglycoside antibiotic selected from the group consisting of xylostasin, ribostamycin, neomycin-group antibiotic, paromomycin-group antibiotic, kanamycin-group antibiotic, 3'-deoxy and 3',4'-dideoxyderivatives of these antibiotics, gentamicin-group antibiotic and lividomycin-group antibiotic are formylated and the amino group at the 1-position is unsubstituted.

2. A compound as claimed in claim 1, namely, 3,2',6'-tri-N-formyl-xylostasin.

3. A compound as claimed in claim 1, namely, 3,2',6'-tri-N-formyl-3'-deoxyxylostasin.

4. A compound as claimed in claim 1, namely, 3,2',6'-tri-N-formyl-3'-deoxyribostamycin.

5. A compound as claimed in claim 1, namely, 3,6',3''-tri-N-formyl-kanamycin A.

6. A compound as claimed in claim 1, namely, 3,2',6'-tri-N-formyl-ribostamycin.

7. A compound as claimed in claim 1, namely, 3,2',6',3''-tetra-N-formyl-kanamycin B.

8. A compound as claimed in claim 1, namely, 3,2',6',3''-tetra-N-formyl-3'-deoxykanamycin B.

9. 3'-deoxybutirosin A.

10. 3'-deoxybutirosin B.

* * * * *